United States Patent [19]
Calabro' et al.

[11] Patent Number: 5,813,767
[45] Date of Patent: Sep. 29, 1998

[54] SYSTEM AND A METHOD FOR MONITORING COMBUSTION AND POLLUTANTS IN A THERMAL PLANT BY MEANS OF LASER DIODES

[75] Inventors: Bruno Calabro'; Luis Frontini, both of Genoa; Francesco Repetto, Cogoleto, all of Italy

[73] Assignee: Finmeccanica S.p.A. Azienda Ansaldo, Italy

[21] Appl. No.: 707,805

[22] Filed: Sep. 6, 1996

[51] Int. Cl.[6] .................................................. G01K 1/08
[52] U.S. Cl. ................................ 374/142; 250/345
[58] Field of Search .................... 374/45, 121, 127, 374/129, 141, 142; 250/339.11, 339.12, 343, 345

[56] References Cited

U.S. PATENT DOCUMENTS

| | | | |
|---|---|---|---|
| 3,902,807 | 9/1975 | Fleming et al. | 356/74 |
| 4,105,919 | 8/1978 | Bridges et al. | 250/343 X |
| 4,161,747 | 7/1979 | Jennings | 357/82 |
| 4,652,756 | 3/1987 | Ryan et al. | 350/343 |
| 4,784,494 | 11/1988 | Pawliszyn | 356/432 |
| 4,829,533 | 5/1989 | Hallberg et al. | 372/29 |
| 4,869,068 | 9/1989 | Van Vloten | 62/51.1 |
| 4,871,251 | 10/1989 | Preikschat et al. | 356/336 |
| 4,940,333 | 7/1990 | Pawliszyn | 356/432 |
| 4,953,477 | 9/1990 | Martin . | |
| 5,024,535 | 6/1991 | Winston, Jr. | 374/178 |
| 5,036,189 | 7/1991 | Geller | 250/205 |
| 5,047,639 | 9/1991 | Wong | 250/343 X |
| 5,185,643 | 2/1993 | Vry et al. | 366/358 |
| 5,188,286 | 2/1993 | Pence, IV | 374/178 X |
| 5,252,060 | 10/1993 | McKinnon et al. | 250/345 X |
| 5,299,869 | 4/1994 | Wissinger | 374/137 |
| 5,301,014 | 4/1994 | Koch | 250/343 X |
| 5,448,071 | 9/1995 | McCaul et al. | 250/343 |
| 5,473,428 | 12/1995 | Lee et al. | 356/345 |
| 5,542,285 | 8/1996 | Merilainen et al. | 250/343 X |
| 5,551,780 | 9/1996 | Wintrich et al. | 374/121 X |
| 5,621,213 | 4/1997 | Barshad | 250/343 X |

FOREIGN PATENT DOCUMENTS

| | | |
|---|---|---|
| 2139043 | 6/1995 | Canada . |
| 0084726 | 8/1983 | European Pat. Off. . |
| 0352620 | 1/1990 | European Pat. Off. . |
| 0661500 | 7/1995 | European Pat. Off. . |

OTHER PUBLICATIONS

M. P. Arroyo et al., *Absorption Measurements of Water–Vapor Concentration, Temperature, and Line–shape Parameters Using a Tunable InGaAsP Diode Laser*, (Applied Optics, vol. 32, No. 30, pp. 6104–6116, Oct. 20, 1993).

D. S. Baer et al., *Multiplexed Diode–Laser Sensor System for Simultaneous $H_2O$, $O_2$, and Temperature Measurements*, (Optics Letters, vol. 19, No. 22, pp. 1900–1902, Nov. 15, 1994).

F. Wittgrefe et al., *Semiconductor Lasers for Spectroscopy*, (Measurement Science & Technology, vol. 2, No. 4, pp. 304–311, Apr. 1991).

*Primary Examiner*—George M. Dombroske
*Assistant Examiner*—Paul D. Amrozowicz
*Attorney, Agent, or Firm*—Sheridan, Ross, P.C.

[57] ABSTRACT

A system for monitoring combustion and pollutants developed in a combustion chamber comprising at least one longitudinal single mode laser diode emitting a beam of electromagnetic radiation with a frequency modulated around the resonance frequency of a specific spectral absorption line of a component of the combustion gases, means for directing the beam into the combustion chamber along a path through the combustion gases to a radiation sensor and processing means connected to the sensor in order to identify the temperature of the combustion gases and the concentration of the component with the specific absorption line by the measurement of the intensity of radiation transmitted at various frequencies in a region surrounding the resonance frequency.

10 Claims, 3 Drawing Sheets

SYSTEM AND A METHOD FOR MONITORING COMBUSTION AND POLLUTANTS IN A THERMAL PLANT BY MEANS OF LASER DIODES

FIELD OF THE INVENTION

The present invention relates to a system and a method for measuring the temperature and the concentration of $O_2$, CO, HCl and other chemical species contained in the flames and in the combustion fumes developed in thermal plants and incineration plants.

The purpose of the measurement is to monitor the combustion/incineration and/or the hot neutralization of the acid substances resulting from the incineration or combustion.

Although the main field of application of the system is that of waste incineration plants, the system can also be used in thermal plants supplied with coal, hydrocarbons or gases resulting from the gasification and pyrolysis of waste, biomasses or other combustibles.

The need to provide systems for measuring and controlling combustion results from the ever greater care taken both in optimizing the combustion process and in controlling pollutant emissions. The use of fuels which are non-homogeneous in form and chemical characteristics, such as urban waste in particular, increases these problems.

STATE OF THE ART

It is in fact known that, in order to achieve complete combustion of the fuel it is necessary to provide an excess of air relative to the stoichiometric combustion ratio, which excess depends upon the physical characteristics of the fuel but reduces the heat yield. Moreover, the excess of air favours the development of toxic substances such as $NO_x$ at high temperatures.

The main parameter which is generally used for monitoring combustion is the temperature in the combustion chamber which is measured with the use of optical pyrometers or video cameras sensitive in the infra-red and visible ranges. These systems have quick enough responses to permit automatic regulation which, however, remains subject to considerable uncertainty. Complementary monitoring of the composition of the combustion fumes is also carried out by the withdrawal, cooling and analysis of suitable samples in suitable analyzers (ORSAT equipment and the like).

The analysis process is relatively slow and is not suitable for controlling combustion if heterogeneous fuels such as urban waste with greatly variable characteristics are used.

Moreover, the standardization of the samples may bring about a considerable difference between the composition of the combustion fumes in their actual situation and the samples analyzed.

Absorption spectroscopy systems have also been proposed for detecting the concentration of some particular pollutant substances in the combustion fumes emerging from the plant.

For example, the document EP-0084726 describes a system for detecting the concentration of $NH_3$ in the fumes of a plant using two $CO_2$ lasers to generate two beams of monochromatic light with a wavelength which is spectrally selectively absorbed by NH, and with a wavelength which is not selectively absorbed, respectively.

The two beams pass through the fumes of the plant along the same active path and the intensity transmitted is detected by sensors which provide an indication of the spectrally selective absorbtion brought by $NH_3$ by means of the difference, corrected in dependence on any different intensity of emission of the two lasers, and cleaned of noise and non spectrally-selective absorption due to the system, to blown ash and the like.

Since absorbtion depends on temperature as well as concentration, a thermoelectric sensor enables the absorption measurement to be corrected according to temperature, and the concentration of NH, in the fumes to be found.

The problem of the absorption depending on the composition of the fumes, that is, of the partial pressures of the various chemical species present is avoided by the assumption that some chemical species are present in concentrations which are variable within predetermined limits, which limits the uncertainty of the measurement.

The document EP-0318752 describes a system similar to that referred to above in which a single $Co_2$ laser is operated to generate, at distinct time intervals, monochromatic light with two wavelengths which are spectrally selectively absorbed and are not absorbed by $NH_3$, respectively.

Although the systems described are effective for identifying and measuring the concentration of a single chemical species, even in hot fumes, they are limited in their application to cases in which the composition of the fumes is only slightly variable but, on the other hand, are not suitable for applications in which the composition is greatly variable, as in the case of incineration plants.

Moreover, they require a temperature measurement carried out with thermometric probes, the precision of the concentration measurement depending on the precision and sensitivity of this temperature measurement which is in any case limited. "In situ" use for detecting several chemical species would be of prohibitive complexity, bulk and cost owing to the need to provide cooling systems, insulation from mechanical and sound vibrations, and continuous control and adjustment of the working point for a plurality of gas lasers which are intrinsically expensive, bulky and require adequate support instrumentation which is also bulky and expensive.

SUMMARY OF THE INVENTION

These limitations are overcome by the monitoring system of the present invention which is simple, compact and extremely precise and can measure the concentration of a chemical species and its temperature with the use of a single source of monochromatic light such as a longitudinal single mode laser diode and, with the use of several sources of monochromatic light, can define a map of fume temperatures in various regions of a combustion chamber and can precisely measure concentrations of several chemical species of interest.

This information is available within very short measurement times of less than 100 msec, enabling combustion to be optimized by the regulation, which may be automatic, of the principal parameters such as primary air, secondary air, and others (such as the sectorizing of the quantity of air in grating furnaces) permitting better control of the most critical regions, reducing excess air, unburnt substances and their contribution to the formation of pollutants to a minimum, optimizing the consumption of reagents used to destroy acid substances such as HCl, HBr, $SO_2$, HF and others, and homogenizing the temperature of the fumes before they pass through the recovery boiler.

The intrinsic advantages of the system are:

high sensitivity and precision (1 ppm, and 1° C.)

speed of measurement (100 ms)

very wide field of measurement absence of moving parts and chemical reagents or catalysts (which are necessary, for example, in conventional analysis equipment)

minimal bulk and ease of transportation and installation, low cost good reliability and zero maintenance.

These results are achieved by a monitoring system according to the invention in which one or more longitudinal single mode laser diodes emit a beam of monochromatic light each with a wavelength close to that of a preselected absorption line specific to a chemical species to be identified and measured quantitatively.

The monochromatic light beam or beams, guided optically by mirrors or optical fibres if necessary, penetrate the combustion chamber through self-cleaning optical windows, pass through the fumes and are collected by one or more sensors which send signals to a processing and control station of the system, which may be a remote station.

The processing and control station imposes on the laser diodes a periodic modulation of the wavelength emitted by the diodes sufficient to scan the entire amplitude of the preselected absorption line so as to detect the complete shape of the absorption line.

From an analysis of the shape of the absorption line carried out by "fitting" procedures, the processing station can discriminate between the "Doppler" or temperature component of the shape of the line and the other components and can identify the concentration of the chemical species by means of the maximum intensity of the Doppler absorption component, and also the temperature of the chemical species and, naturally, of the fumes of which it forms part, by means of the width of the Doppler component of the line.

Unlike known measurement methods which are based on the recognition of two absorptions with different wavelengths, the measurement method., which is based on a "fitting" operation and hence analysis of the complete shape of an absorption line, is made possible by the use of longitudinal single mode laser diodes which have a wide tuning range of the order of tens of GHz associated with a very narrow line width emitted of the order of one MHz which, can be further reduced by suitable measures.

The frequency emitted by the laser diodes can easily be varied and controlled by the modulation of the supply current and the temperature of the working point can easily be stabilized by simple and compact thermostatic systems.

The devices can also be isolated easily and cheaply from noise and vibrations which are always present to a considerable extent in combustion plants.

SHORT DESCRIPTION OF THE DRAWINGS

The characteristics and advantages of the system and method of the present invention will become clearer from the following description and from the appended drawings, in which.

DETAILED DESCRIPTION

Figure 1:
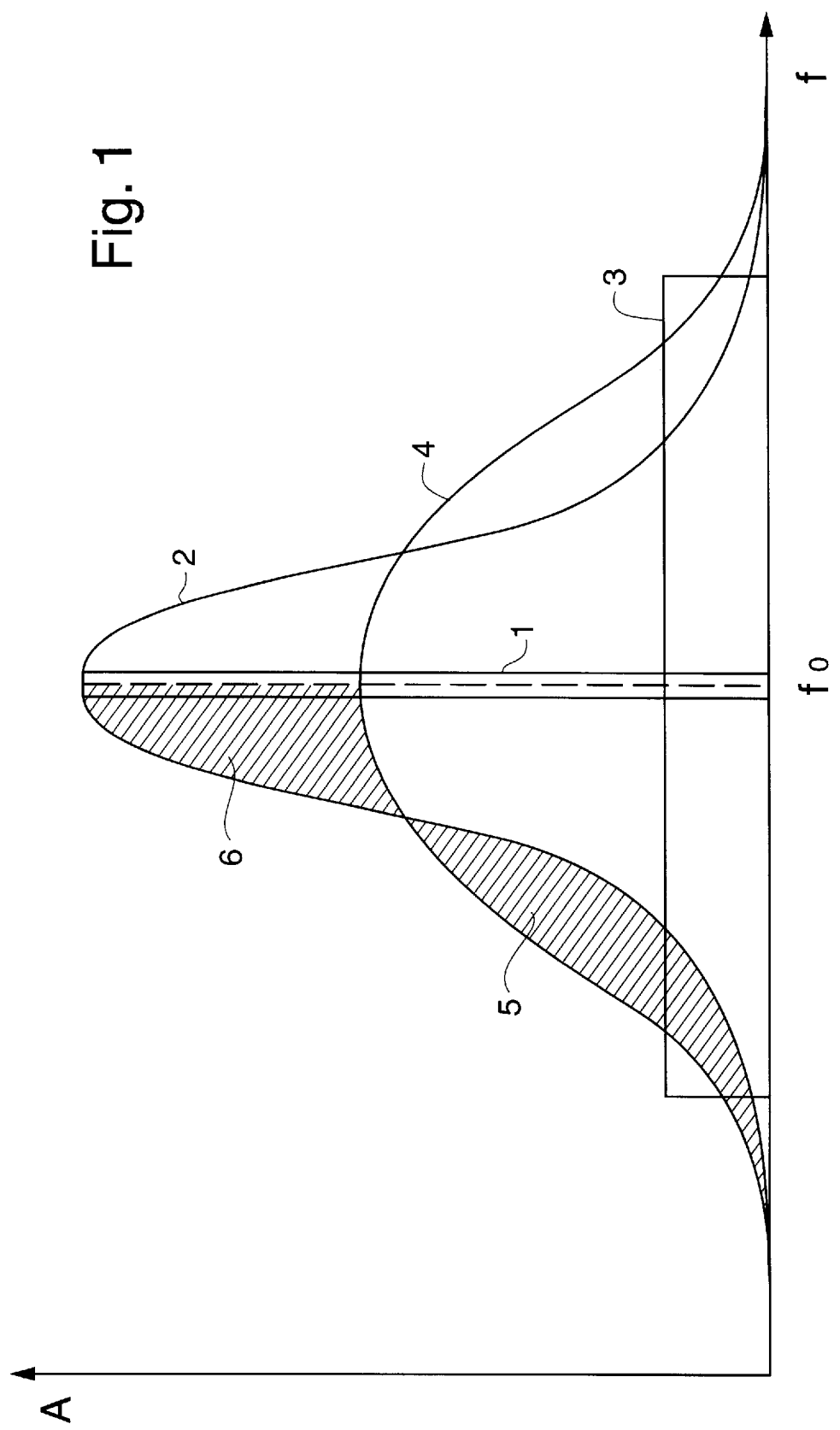
FIG. 1 shows qualitatively in a graph of absorption (A)/frequency f (or pulsation ω) the various components which determine the shape of a spectral absorption line.

Before describing the monitoring system and the method of the present invention, it is appropriate to set out some considerations of a general character beforehand.

It is known that the absorption lines of an absorption spectrum for a predetermined chemical species are not actually lines corresponding to a predetermined frequency but absorption bands extending around a predetermined frequency or resonance frequency with a shape and width which depends on various factors.

Monitoring the "natural" broadening which leads to a homogeneous band width of equal amplitude of the order of hundreds of Hz, the factors which contribute most to the shape and width of the absorption band are:

1) Doppler broadening

In a gas, the molecules have different velocities with different orientations relative to a common reference such as a light source.

The velocities have a Gaussian distribution depending on the gas temperature,

This distribution causes, by the Doppler effect, a corresponding distribution in the frequencies at which the molecules or atoms can absorb the photons.

The absorption lines therefore assume a bell-like Gaussian shape the width of which is greater the higher the temperature.

The shape of the absorption line is described by the function $$I + Io \exp\left[ -\frac{M \cdot C^2 \cdot \Delta\omega^2}{2K_o T \omega_2} \right]$$

where

C=the speed of light

Δω=the deviation from the resonance frequency expressed in pulsations (Δω=2 ΠΔf).

$K_o$=the Boltzman constant

T is the absolute temperature

ω is the independent variable

M is the molecular mass

From this function it is easy to derive the width of the absorption line, which is proportional to the square root of the absolute temperature and, although proportionally variable with the frequency and dependent on the molecular mass, at ambient temperature and in the range of absorption frequencies corresponding to wavelengths between 1 and 2 μm, is of the order of hundreds of MHz and much greater than the natural broadening.

For example, in the range of wavelengths between 1 and 2 μm $NH_3$ and $H_2O$ molecules have Doppler widths of 400 and 150 MHz respectively at ambient temperature and at the respective resonance frequencies and these are approximately doubled at a temperature of 800°–900° C.

2) Broadening owing to "collision" or to "pressure"

When the molecules of a gas or of a mixture of gases move, their motion brings them towards one another and they interact causing a change in their energy and vibration states with an equal probability that the molecules will assume an energy level which differs from that before the collision by any value between ±E where E depends upon the pressure, the temperature and other factors; this causes a homogeneous broadening of the absorption line which, by this effect alone, that is, in the absence of a DOPPLER effect, assumes the shape of an equi-absorption band, or Lorenztian function centred on the resonance frequency and having an amplitude H defined by $H=1/\Delta v_L$ and a width $\Delta v_L$ defined in short by the equation $$\Delta v_L = K(T, P_1, P_2 \ldots P_N) \cdot P$$

where $\Delta v_L$ is the broadening owing to collisions expressed as wavelength, K(T, $P_1$, $P_2$ . . . $P_N$) is a variable coefficient depending upon the temperature T and the partial pressures $P_1$ . . . $P_N$ of the various chemical species constituting the gaseous mixture and P is the total pressure.

This further broadening is combined with the Doppler contribution (on all of the lines which make up the absorption spectrum determined by the Doppler effect) and the resulting effect on the shape of the absorption line is that it assumes a Voight profile, that is, a profile of the convolution or integral product of the Gaussian function and of the Lorentzian function.

FIG. 1 shows qualitatively in a graph of absorbency A/frequency the natural shape of an absorption line 1 centred on a resonance frequency $f_o$, the shape resulting from the Doppler effect alone (Gaussian curve 2), the shape resulting from the broadening owing to pressure alone (Lorentzian curve 3) and the Voight profile 4 resulting from the accumulation of the effects.

As can be seen, the absorbency of the absorption line is considerably attenuated at its peak value and is spread more uniformly.

The broadening owing to collisions dominates at atmospheric pressure where it is of the order of 1 GHz and more, that is, of an order of magnitude greater than the Doppler contribution, whereas at low pressures of the order of 5–10 Torr there is practically only the Doppler contribution.

Whilst the Doppler broadening for a given chemical species and resonance frequency depends solely on temperature, the broadening owing to collisions depends not only upon the pressure but also, and to a considerable extent, on the temperature and the composition of the gaseous mixture.

Since the peak absorption value depends on the broadening owing to collisions (the areas 5 and 6 of FIG. 1 should be equal) it is virtually impossible to identify the concentration of a chemical species by an absorption peak measurement in the presence of other chemical species without knowing their concentrations, and hence partial pressures, and the temperature.

It is clear, however, that if the entire shape of the Voight profile (or at least half of it) can be detected it is possible, by analytical processing or fitting methods to identify the equation of the particular Gaussian curve which, combined with a Lorentzian curve, produces the Voight profile shape detected.

The identification of this Gaussian curve defines its width and its amplitude (peak value).

By the measurement of the width, which is due solely to the Doppler contribution and therefore for a given resonance frequency and chemical species depends solely on temperature, it is possible to calculate the temperature.

The amplitude, on the other hand provides a measurement of the absorbency A of the chemical species, cleaned of the broadening effects due to pressure.

The absorbency A thus corrected enables, by means of the known Beer Lambert law which links transmissivity to concentration:

$$I = I_o \cdot e^{-\sigma(\psi)NL}$$

where $I_o$ = intensity of incident radiation

I = intensity of radiation transmitted $\sigma(\omega)$ = specific parameter of the chemical species considered, variable with frequency ($f=\omega/2\Pi$)

N = concentration

L = length of absorption path, enables as said the concentration N of the chemical species monitored to be determined.

In fact $A=(I_o-I)/I_o=1-e^{\sigma(\omega)NL}$

This measurement, which is based on the recognition of the shape of the absorption spectrum, is independent of the pressure and composition and minimizes errors resulting from noise and interference which, to have a significant effect on the accumulation of the measurements, would have to have a Gaussian distribution in the spectrum of frequencies examined.

In order to implement this method in an industrial context, such as an incineration plant or a thermal plant, it is necessary to have available one or more sources of monochromatic light of extreme spectral purity and with a frequency which is adjustable continuously and repetitively throughout the range of frequencies affected by the Voight profile relating to an absorption line to be analyzed. As already stated, the spectral width of the emission should be of the order of a few MHz or less and the frequency adjustability should extend to a few GHz. The light source should have an intensity which is known even if it is not necessarily constant at the various scanning frequencies and should be insensitive to vibrations and noise.

The structures for the installation of the light source and the control equipment should be simple, cheap and compact.

These requisites, together with those of good reliability and compactness are satisfied by laser diodes emitting in longitudinal single mode, of the type used for telecommunications.

Laser diodes with emission in the red wavelength band (0.6–0.7 $\mu$m; InGaP diodes) and in the near infra-red bands (0.7–0.9 $\mu$m: GaAlAs diodes; 1–2 $\mu$m: InGaAsP diodes) are already on the market.

The emission spectra of these diodes cover a frequency band in which secondary absorption bands or lines of the chemical species of interest in the monitoring of concentrations of fumes are present and which are therefore less intense than the fundamental bands, possibly by two orders of magnitude.

This fact, which considerably limits the sensitivity of measurements effected by conventional techniques does not, however, substantially adversely affect the precision achievable by the method described.

Figure 2:
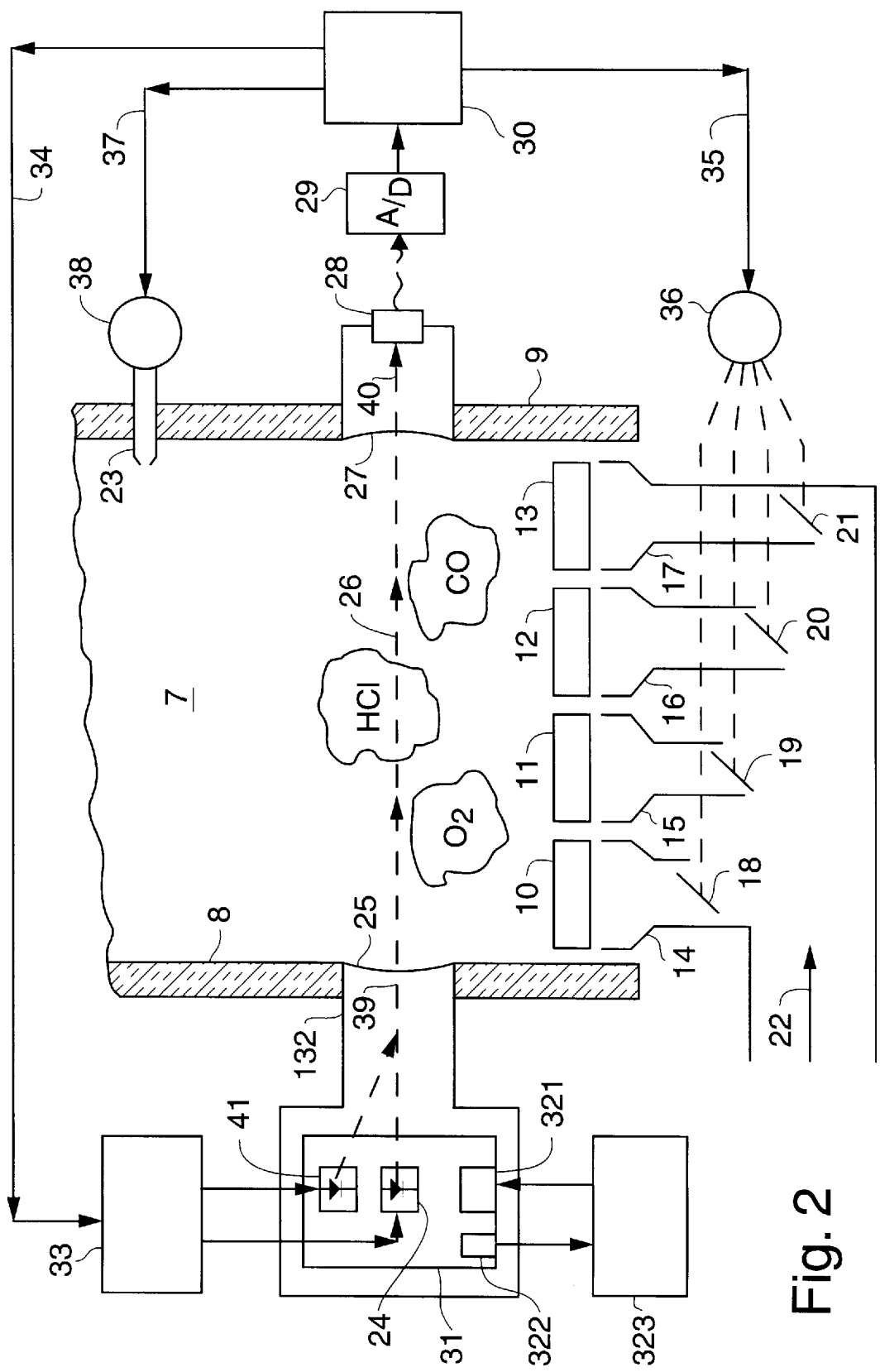
FIG. 2 shows schematically a preferred embodiment of the monitoring system according to the present invention, applied to a incinerator with a grating.

FIG. 2 shows, in generally schematic form, a system for monitoring the temperature of fumes applied to an incineration plant, for example, of the type with a grating.

The incineration plant comprises a combustion chamber 7 surrounded by refractory walls 8, 9, at the base of which a sectorized grating 10, 11, 12, 13 transports the fuel constituted by waste to be incinerated.

Air inlet ducts 14, 15, 16, 17 choked by regulating shutters 18, 19, 20, 21 admit a suitable flow of combustion air 22 to the combustion chamber 7 through the grating and the bed of waste.

As a result of the combustion, acid substances, particularly HCl, are developed in the fumes and, in order to destroy these, a suitable flow of a basic substance, preferably CaCo$_3$ powder, is admitted to the combustion chamber, for example as described in European patent application EP-A-0605041.

The admission takes place by means of suitable nozzles 23.

The temperature of the fumes is normally monitored by thermometric probes, the indications of which are used by regulation systems to act appropriately on the shutters 18, . . . 21 and/or to activate auxiliary burners, not shown, so as to keep the temperature of the fumes within a predetermined range, for example 850°–950° C.

It is also desirable to measure the concentration of HCl in the fumes in order to regulate the flow of basic substance appropriately so as to achieve an optimal destruction of HCl with the minimum consumption of basic substance.

In order to measure the HCl concentration and the temperature jointly, the incineration plant is equipped with a monitoring and regulation system which comprises a laser diode 24 with longitudinal single mode emission which sends a monochromatic radiation beam into the combustion chamber 7 through an optical window 25, which is preferably self-cleaning, formed in the wall 8 of the furnace.

The beam passes through the fumes along an absorption path 26 and, through an optical window 27 formed in the wall 8 opposite the wall 9, strikes a radiation sensor 28 spectrally sensitive to the radiation emitted by the diode 24.

The analog signal emitted by the sensor 28 is sent to an A/D converter 29 and from there to a processing and control unit 30.

To avoid direct exposure of the diode 24 and the sensor 28 to the temperatures of the furnace, these may also be installed in positions remote from the furnace walls and the light beam may be conveyed from the diode 24 to the optical window 25 by means of an optical guide 39, in air, inert gas or optical fibre and, from the optical window 27 to the sensor 28 by equivalent means 40.

Alternatively, to reduce the number of passages through the furnace walls, the optical window 27 may consist of a mirror which sends the incident beam back towards the optical window 25 and through it to the sensor 28.

The length of the optical path is thus doubled and the sensitivity of the measurement system increased.

This can be further increased, within certain limits, by multiple reflections.

Since the spectral purity of the radiation emitted by the diode 24 is affected by sound vibrations of both low and high frequency, the diode 24 is fitted on an antivibration support 31 enclosed in a suitable housing 132.

The support 31 which is advantageously of material with high thermal conductivity such as copper, is kept at a temperature controlled precisely by a temperature regulation system comprising a Peltier cell 321 connected to the support, a resistive temperature-measurement bridge 322 and a supply 323 for the Peltier cell, controlled by feedback of the temperature measurement.

A controlled supply 33 supplies the diode 24 with a predetermined current supply variable according to predetermined periodic laws, for example, with periodic sawtooth, triangular or even sinusoidal slopes with periodicity of the order of 10–20 ms corresponding to a frequency of 50–100 Hz.

As is known, the intensity and frequency of the radiation emitted by a laser diode vary in dependence on the supply current, in known manner.

With a constant temperature ensured by the temperature control system, it is therefore possible to correlate a predetermined emission intensity Io and a predetermined wavelength of the radiation emitted with each predetermined supply current.

There is no difficulty in obtaining continuous excursion ranges of the wavelength of radiation emitted of the order of 10 GHz and even more from a longitudinal single mode laser diode such as DFB (distributed feedback) or DBF (distributed Bragg reflector) diodes.

The average emission frequency of the diode 24 is selected so as to correspond to a spectral absorption line of a chemical species to be determined (in the example described, HCl) which is advantageously distant from other spectral absorption lines of the same chemical species or of other chemical species which may be present in the fumes, such as CO, CO$_2$, H$_2$O, SO, N, O$_2$ to prevent interference between adjacent absorption lines. Purely by way of example, in the case of HCl, the absorption line corresponding to the second overtone at 1207.9 nm may be selected.

As already stated, by varying the emission frequency of the laser continuously around the wavelength of 1207.9 nm it is possible to detect, by means of the sensor 28, the shape of the absorption line throughout a region surrounding the nominal wavelength corresponding to the resonance frequency selected.

The signal emitted by the sensor 28 is sampled and converted into digital form with a suitable period, for example 10 $\mu$s, by an A/D converter 29. The binary code output by the converter 29, which is indicative of the transmissivity of the optical path 26, is sent to the processing unit 30.

The unit 30 preferably but not necessarily sends suitable synchronization signals to the regulation system 33 by means of wires 34 so that the emission intensity of the diode 24 at the time, which is variable with the supply current, is known.

The data received in chronological succession by the processing unit 30 via the A/D converter 29 are corrected by the unit 30 in dependence on the variable intensity emitted and are stored. They are representative of the absorption detected point by point throughout the band of the absorption line.

If, as stated, the scanning takes place in 10 ms and the sampling of the signal has a periodicity of 10 $\mu$s, 1000 measurements which precisely describe the shape of the absorption line are collected and stored.

By an examination of the data collected, the processing unit 30, suitably programmed, can identify by known "fitting" techniques or even differential analysis, the Gaussian component of the shape of the absorption line detected and hence the temperature of the fumes and the concentration of HCl along the optical path as well as the background absorption or noise of the detection system.

Unlike measurement systems which reduce random measurement errors, but not systematic errors, to a minimum by repetition of the measurement under the same conditions, the method implemented also minimizes systematic errors.

It is possible to establish an analogy between the method implemented and holographic techniques; a hologram of an object is the description of the image of an object by a representation of each point of the image distributed at each point of the hologram according to predetermined optical laws.

It is possible, by the same optical laws, to reconstruct the initial image, but a single error occurring in the reconstruction in the formation of a point of the hologram, like the accumulation of single errors, has a negligible effect on the image reconstructed.

These affect the reconstructed image only if the errors are distributed according to a law which interferes with the optical laws used in the generation and reconstruction of the hologram.

In the present case, the shape of the absorption line is determined according to physical laws such as the convolution of a Gaussian curve and of a Lorentzian curve and, by the application of these laws, it is possible to derive from the plurality of measurements the Gaussian component and its characteristics parameters even if the single measurements are affected by errors. The only errors which affect the reconstruction of the Gaussian curve are errors distributed, in dependence on the wavelength, by Gaussian laws; that is not the case for the measurement errors due to noise or to sensitivity limits of the detection system.

It is therefore clear that, after a period for the collection of data which, by way of indication may be 10 ms, and a processing time which is also very short and of the order of a few tens of milliseconds, the processing unit 30 can provide a precise joint measurement of temperature and concentration even with the use simply of a personal computer with limited calculating power.

By comparing the temperature detected with a desired temperature, the processing unit 30 can generate an error signal (analog or digital) which is transferred by means of wires 35 to a regulation member 36 for the opening/closure of the shutters 18 . . . 21 and/or the control of auxiliary burners.

The indication of the HCl concentration can be converted by suitable laws into a control signal sent through wires 37 to a member 38 for regulating the flow of basic substance which is admitted to the combustion chamber.

Clearly, with the use of a plurality of laser diodes such as 24, 41 operating at different frequencies, each linked with an absorption line of a different chemical species, it is possible to identify the concentrations of various chemical species of interest, such as $CO$, $O_2$, $SO_2$, $NH_3$.

As shown in FIG. 2, the radiation emitted by the various diodes can be conveyed along the same optical path or along adjacent optical paths through the same optical input and output windows so as to reduce the number of penetrations to a minimum.

The recognition can be carried out by a plurality of sensors such as 28, each associated with a diode, or even by a single wide-spectrum detection sensor.

In this second case, electro-optical switches or rotating mechanical obturation devices enable the radiation emitted by each diode to pass through the window 25 in different and successive time periods.

The use of a plurality of diodes and sensors arranged so as to form a plurality of optical paths in the combustion chamber, which are at least partially distinct and possibly intersecting, permits the detection of the concentration of several chemical species and, at the same time, a temperature map of the combustion chamber by means of which to regulate the combustion by selective action on the primary air control shutters and/or on a plurality of auxiliary burners, or even on shutters for deflecting the fumes output by the combustion chamber to optimize the distribution of the thermal flow through the recovery boiler.

In this case it is also possible to make use of a number of sensors smaller than the number of laser diodes, the various transit paths which are made to converge on the sensors being enabled selectively by means of shutters. Clearly a concentration map of the same or several chemical species can also be detected.

Figure 3:
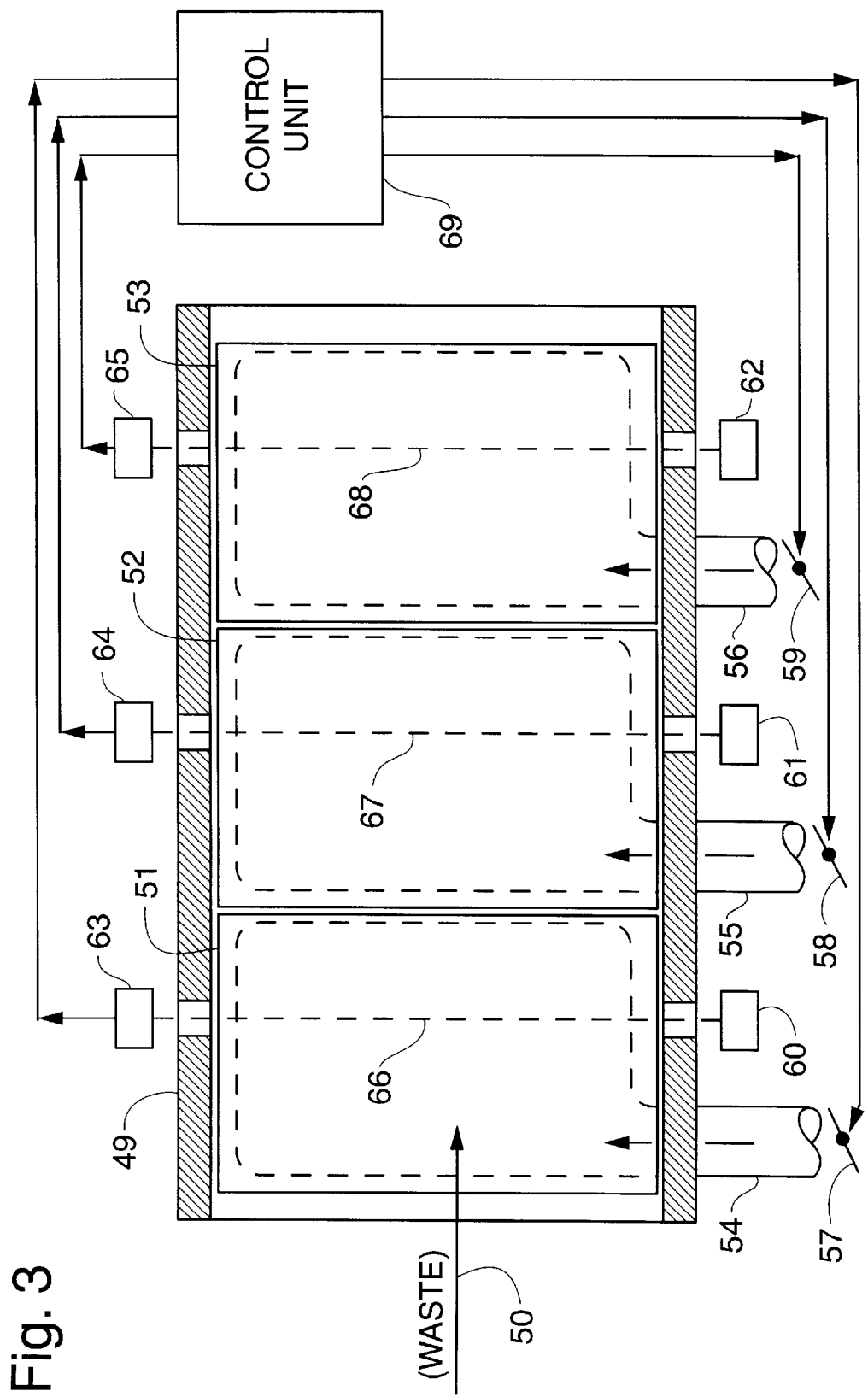
FIG. 3 shows schematically an embodiment of the monitoring system according to the present invention, applied to a incinerator with a sectorized grating, for mapping the temperature and $O_2$ concentration in the combustion chamber in order to optimize the combustion by selective control of the grating sectors.

To better explain the advantages and opportunities resulting from temperature and concentration mapping FIG. 3 shows, in schematic top view, the combustion chamber 49 of a waste incinerating plant where fuel constituted by waste is admitted in the direction indicated by arrow 50 and transported by grating sectors 51, 52,53 through the combustion chamber.

Air inlet ducts 54,55,56, individually chocked by regulating shutters 57,58,59, admit a suitable flow of combustion air to the combustion chamber, through the grating and the bed of waste.

A plurality of laser diodes 60,61,62 and related sensors 63,64,65, (not necessarily in the same nuber of the laser diodes), form a plurality of distinct optical path 66,67,68, in the combustion chamber, for the radiation emitted by the laser diodes, each related to a particular section of the chamber receiving combustion air from a predetermined one of the air inlet ducts 54,55,56.

The laser diodes and related sensors allows to measure the flue gas temperature along the different optical paths as well as the $O_2$ concentration along the same optical paths.

A bidimensional map of temperature and $O_2$ concentration is thus obtained which can be used by a control unit 69 to individually and selectively control the regulating shutters 57,58,59 to optimize the combustion process.

It is clear that, although the identification method described is preferable owing to its precision and immunity to interference, less precise analytical methods may be used.

For example, if the changes in concentration of the various components of the fumes have a negligible effect on the broadening of the absorption line and compensate for one another and the width of the absorption line can therefore be considered to depend solely on the temperature, it is possible, by a frequency scanning method, to identify the band width and to derive the temperature therefrom, possibly with the measurement of the pressure in the combustion chamber if this differs significantly from atmospheric pressure.

It is then possible, with the measurement approximations to which the cited document EP-0084726 refers, to identify the concentration of the chemical species purely on the basis of the measurement of the absorption peak.

In particular, in the case of a monitoring system in which a plurality of laser diodes is used, in order to recognize the concentration of different chemical species, if temperature mapping is not required, all of the diodes except one may operate at frequencies linked with the respective absorption lines in order to measure solely the amplitude of the absorption peak and possibly the zero level or background absorption level.

This latter indication, with the necessary corrections due to the possible difference in intensity may be supplied by the laser diode which has the task of measuring the temperature by frequency scanning.

We claim:

1. A system for monitoring a combustion process with the development of pollutant substances in the combustion fumes in a combustion chamber, comprising:

at least one longitudinal single mode laser diode emitting radiation at a wavelength corresponding to that of a predetermined spectral absorption line of a predetermined chemical species, modulation means for periodically modulating the wavelength of radiation emitted in a region surrounding that of said absorption line, conveyor means for directing the radiation along a transit path through the combustion chamber, collector means for receiving a fraction of the radiation which has not been absorbed along the transit path and for conveying it to detection means comprising at least one radiation sensor, the radiation sensor generating a signal correlated to the intensity of the radiation fraction, and processing means connected to the detection means for identifying jointly, in dependence on the signal received by the detection means, sampled at successive moments and describing the shape of said spectral absorption line, the temperature of the combustion fumes passed through along the transit path and the concentration of the predetermined chemical species.

2. A monitoring system according to claim 1, comprising regulation means connected to the processing means for controlling a parameter of the combustion process in dependence on the temperature identified by the processing means.

3. A monitoring system according to claim 1, comprising regulation means connected to the processing means (30) for controlling a parameter of the combustion process in dependence on the concentration identified by the processing means.

4. A monitoring system according to claim 1, comprising first regulation means connected to the processing means for controlling a first parameter of the combustion process in dependence on the temperature identified by the processing means and second regulation means connected to the processing means for controlling a second parameter of the combustion process in dependence on the concentration identified by the processing means.

5. A monitoring system according to claim 1, comprising at least one second laser diode emitting radiation at a wavelength corresponding to that of a specific spectral absorption line of a second predetermined chemical species, means for directing the radiation emitted by the second laser diode into the combustion chamber and detector means for generating a second signal, correlated to the intensity of the fraction of radiation emitted by the second laser diode which is not absorbed in the combustion chamber, the second signal being supplied as an input to the processing means and processed by said processing means to identify the concentration of the second chemical species in the combustion chamber.

6. A monitoring system according to claim 1, comprising a thermally conductive anti-vibration support for the at least one laser diode and means with Peltier cells for regulating the temperature of the anti-vibration support.

7. A monitoring system according to claim 5, comprising an anti-vibration support for the at least one longitudinal single mode laser diode and the second laser diode and means with Peltier cells for regulating the temperature of the anti-vibration support.

8. A system for monitoring and controlling a combustion process with the development of pollutant substances in the combustion fumes in a combustion chamber where air is admitted through a plurality of air inlet ducts individually choked by regulating shutters, comprising:

a plurality of longitudinal single mode laser diodes, all emitting radiation at a wavelength corresponding to that of a predetermined spectral absorption line of a predetermined chemical species, modulation means for periodically modulating the wavelength of radiation emitted in a region surrounding that of said absorption line, conveyor means for directing the radiation emitted by each of said laser diodes along a different one of a plurality of transit paths, at least partially distinct, through the combustion chamber, collection means for receiving a fraction of the radiation which has not been absorbed along the transmit paths and for conveying it to detection means comprising at least one radiation sensor, the radiation sensor generating a single correlated to the intensity of the radiation fraction, and processing means connected to the detection means for identifying jointly, in dependent on the signal received by the detection means, sampled at successive moments and describing the shape of said spectral absorption line, a temperature map of the combustion fumes passed through along the transit paths and a concentration map of the predetermined chemical species, and control means responsive to said processing means for individually and selectively controlling said shutters to optimize said combustion process in dependence of said identified temperature map.

9. A method for the joint determination of temperature and concentration of a chemical species in a mixture of gases, consisting essentially of:

passing, through a volume of the mixture of gases, a beam of electromagnetic radiation of known intensity and high spectral purity with a frequency modulated around the frequency of a single specific absorption line of the chemical species, the absorption line comprising a Gaussian component, measuring the absorption of the radiation in the volume at the various frequencies in order to derive the spectral distribution of the absorption of said single specific absorption line, identifying the Gaussian component of the spectral distribution, the corresponding temperature determined by the Gaussian component, and the concentration of the chemical species.

10. The system of claim 8 wherein said combustion chamber has sections each receiving combustion air from a predetermined one of said inlet ducts, each of said transit paths being related to a different one of said sections.

* * * * *

UNITED STATES PATENT AND TRADEMARK OFFICE
CERTIFICATE OF CORRECTION

PATENT NO. : 5,813,767
DATED : September 29, 1998
INVENTOR(S) : Calabro' et al.

It is certified that error appears in the above-identified patent and that said Letters Patent is hereby corrected as shown below:

Cover page at Item 30, please add the following:

-- [30] Foreign Application Priority Data
September 29, 1995 [EPO] European Patent Office 95830401--.

Signed and Sealed this

Fourth Day of May, 1999

Attest:

Q. TODD DICKINSON

*Attesting Officer*   Acting Commissioner of Patents and Trademarks